(12) United States Patent
Chen et al.

(10) Patent No.: US 10,081,653 B2
(45) Date of Patent: Sep. 25, 2018

(54) METHOD FOR PREPARING 6-AMINOHEXYL LACTOSIDE-NOTA CONJUGATE

(71) Applicant: Institute of Nuclear Energy Research, Atomic Energy Council, Executive Yuan, R.O.C., Taoyuan (TW)

(72) Inventors: Rui-Yu Chen, Taoyuan (TW); Yan-Feng Jiang, Taoyuan (TW); Mei-Hui Wang, Taoyuan (TW); Jen-Tsung Wang, Taoyuan (TW); Wuu-Jyh Lin, Taoyuan (TW)

(73) Assignee: INSTITUTE OF NUCLEAR ENERGY RESEARCH ATOMIC ENERGY COUNCIL, EXECUTIVE YUAN, R.O.C, Taoyuan (TW)

( * ) Notice: Subject to any disclaimer, the term of this patent is extended or adjusted under 35 U.S.C. 154(b) by 293 days.

(21) Appl. No.: 15/214,675

(22) Filed: Jul. 20, 2016

(65) Prior Publication Data

US 2017/0183372 A1 Jun. 29, 2017

(30) Foreign Application Priority Data

Dec. 25, 2015 (TW) .............................. 104143830 A

(51) Int. Cl.
*C07H 15/26* (2006.01)
*A61K 49/00* (2006.01)
*C07H 1/00* (2006.01)

(52) U.S. Cl.
CPC ......... *C07H 15/26* (2013.01); *A61K 49/0002* (2013.01); *C07H 1/00* (2013.01)

(58) Field of Classification Search
CPC ....... C07H 15/26; C07H 1/00; A61K 49/0002
See application file for complete search history.

(56) References Cited

U.S. PATENT DOCUMENTS

2011/0077386 A1* 3/2011 Lee .................. C07H 15/04
536/17.9

FOREIGN PATENT DOCUMENTS

TW I392511 B 4/2013

OTHER PUBLICATIONS

Feng (Carbohydrate research 346, (2011), 2650-2662).*
K. P. Ravindranathan Kartha et al., A Simplified, One-Pot Preparation of Acetobromosugars from Reducing Sugars, Journal of Carbohydrate Chemistry, 1990, 777-781, vol. 9, Issue 5.
Paul H. Weigel et al., Preparation of 6-aminohexyl d-aldopyranosides, Carbohydrate Research, 1979, 83-91, vol. 70.
Jianhao Feng et al., Synthesis of a Forssman antigen derivative for use in a conjugate vaccine, Carbohydrate Research, 2011, 2650-2662, vol. 346.

* cited by examiner

*Primary Examiner* — Pancham Bakshi
(74) *Attorney, Agent, or Firm* — Locke Lord LLP; Tim Tingkang Xia, Esq.

(57) ABSTRACT

The present invention provides a method for preparing a 6-aminohexyl lactoside-NOTA conjugate. The preparation method comprises brominating perbenzoylated lactose with hydrobromic acid; glycosylating 6-azidohexanol to obtain 6-azidohexyl perbenzoyl lactoside; and deprotecting this precursor in two steps to obtain 6-aminohexyl lactoside and conjugating 6-aminohexyl lactoside to NCS-benzyl-NODA GA (i.e. 2,2'-(7-(1-carboxy-4-((4-isothiocyanate benzyl) amino)-4-oxobutyl)-1,4,7-triazonane-1,4-diyl) diacetic acid) in triethyl amine as an alkaline solvent, to obtain a 6-aminohexyl lactoside-NCS-benzyl-NODA GA conjugate. In this novel preparation method, no deglycosylated side product is produced, such that the yield is considerably increased to 46%. Therefore, the method is suitable for future massive production since the requirement for repeated preparations for massive production is reduced, and the impurities produced in the previously scaled-up preparation process are not present.

9 Claims, 1 Drawing Sheet

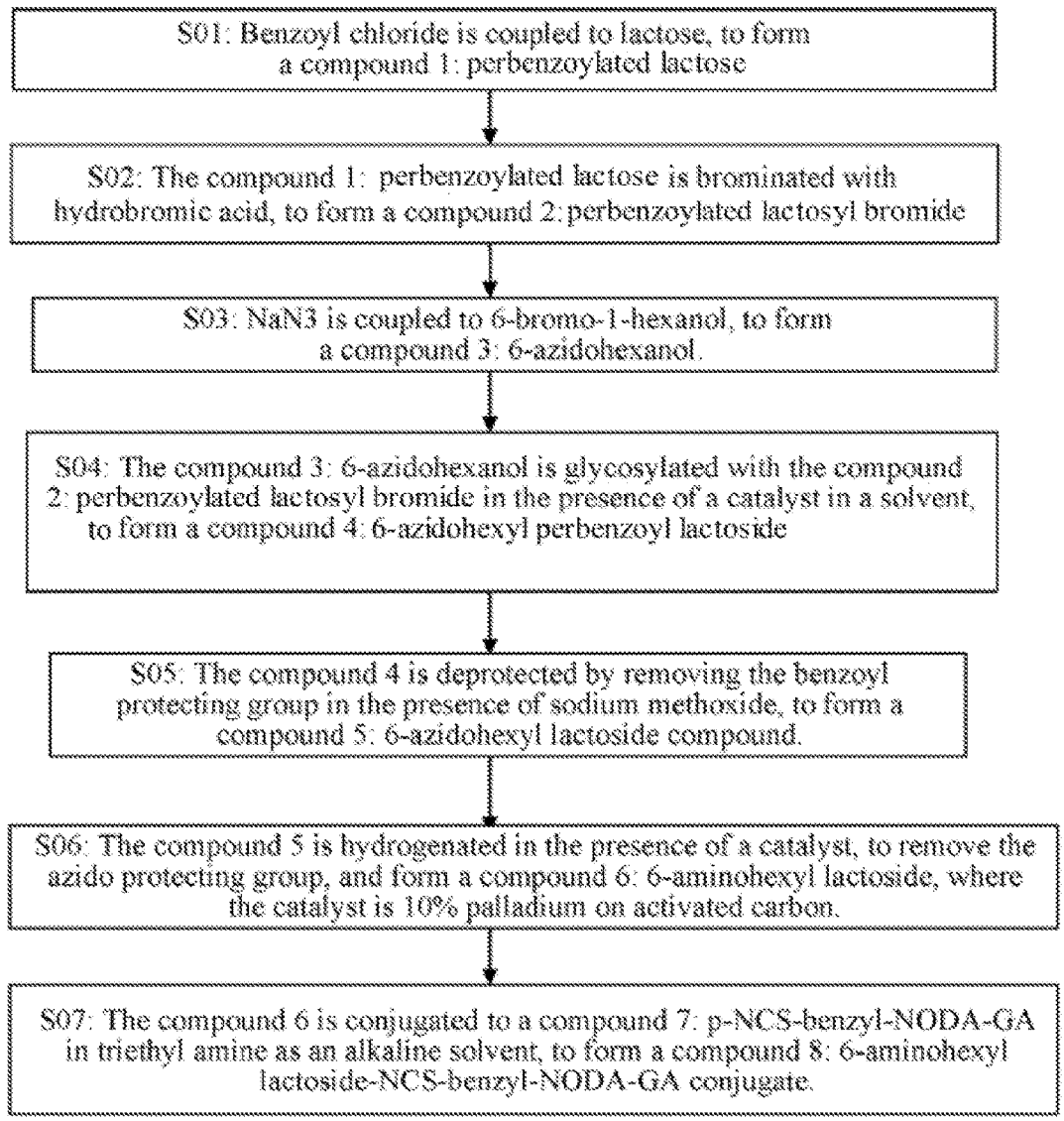
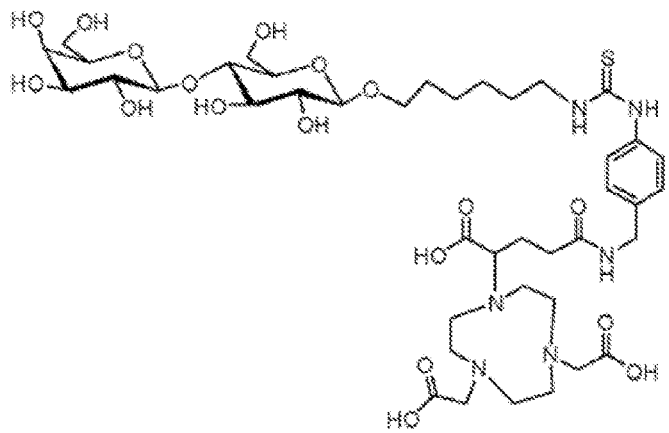

US 10,081,653 B2

METHOD FOR PREPARING 6-AMINOHEXYL LACTOSIDE-NOTA CONJUGATE

CROSS-REFERENCE TO RELATED APPLICATION

This application also claims priority to Taiwan Patent Application No. 104143830 filed in the Taiwan Patent Office on Dec. 25, 2015, the entire content of which is incorporated herein by reference.

TECHNICAL FIELD

The present disclosure relates to a method for preparing a 6-aminohexyl Alactoside-NOTA conjugate, which comprises specifically: reacting perbenzoylated lactosyl bromide with 6-azidohexanol in the presence of AgOTf as a catalyst in dichloromethane as a solvent to glycosylate 6-azidohexanol, then deprotecting in two steps including removing the benzoyl protecting group through reaction in the presence of sodium methoxide, and removing the azido protecting group through hydrogenation in the presence of palladium on carbon, to form 6-aminohexyl lactoside, and then conjugating 6-aminohexyl lactoside to p-NCS-benzyl-NODA-GA (2,2'-(7-(1-carboxy-4-((4-isothiocyanatobenzyl)amino)-4-oxobutyl)-1,4,7-triazonane-1,4-diyl)diacetic acid) in triethyl amine as an alkaline solvent, to obtain a 6-aminohexyl lactoside-p-NCS-benzyl-NODA-GA conjugate.

BACKGROUND

A particular receptor present on the surface of normal hepatocytes has strong binding with glycopeptides bearing terminal lactosyl or galactosyl group. By virtue of this property, 6-aminohexyl lactoside or 6-aminohexyl galactoside derivative conjugated complex is used as imaging agent for targeted receptors on hepatocytes (TWI 392511). The conventional method for preparing 6-aminohexyl lactoside comprises preparing acetobromo β-lactose in one step following the method described by Kartha (J Carbo Chem 9, 777-781, 1990), and preparing 6-trifluoroacetylaminohexyl β-lactoside following the method described by Weigel et al (Carbohydr Res 70, 83-91, 1979.). Briefly, β-lactose is treated with acetic anhydride and HBr/HOAc in a flask; and after acetobromo β-lactose is formed, the amount of the solvent is reduced, and diethyl ether is added for recrystallization, upon which acetobromo β-lactose as beautiful crystal is formed. Subsequently, 6-trifluoroacetylaminohexanol is reacted with acetobromo β-lactose with mercury cyanide as a catalyst, in toluene-nitromethane (1:1 by volume), to produce 6-trifluoroacetylaminohexyl β-lactoside.

The method for removing the acetyl group on acetyl β-lactose includes reacting the compound with a 10 mM solution of sodium methoxide in absolute ethanol for 2 hrs to remove the acetyl group, neutralizing the reaction product with acidic Dowex 50, and evaporating and drying the filtrate.

The method for removing the trifluoroacetyl group includes reacting overnight with 10% ethanol and 10% TEA (triethylamine) at room temperature. The mixture is suction dried, and the residue is then dried in a vacuum desiccators containing excessively amount of sodium hydroxide particles and concentrated sulfuric acid. To remove the counter ions of amino group, the residue is dissolved in 50% ethanol and passed through Dowex 1 ($H^+$ type), until the liquid on the surface becomes basic. After filtering, the filtrate is suction dried.

The conventional glycosylation process of 6-aminohexanol includes acetylating lactose with acetic anhydride in the presence of pyridine.

Briefly, lactose (1.0 equiv, 20.0 g, 58.4 mmol) is added to a 500 mL reaction flask, a stirrer was placed, and then pyridine (180 mL) was added. The solution is stirred while in an ice bath, and acetic anhydride (12 equiv, 88 mL, 87.6 mmol) is added and stirred. After the reaction was complete as detected by TLC (upon which the solution appears clear and yellow), the solution is transferred to an extractor, and EtOAc (500 mL) was added. The impurities in the organic phase are removed by washing with 1 M $HCl_{(aq)}$ (400 mL×4), $NaHCO_{3(aq)}$ (200 mL×2), distilled water (200 mL), and saturated saline (200 mL).

It can be known from above that a 500 mL reaction flask and a 1 L extractor are needed for acetylating 20 g of starting lactose. However, as a result, deglycosylation generally occurs during deprotecting lactose by removing the acetyl group, such that the purification is difficult and the yield of the end product is low. Where the preparation process is scaled up, a quite large glass vessel and more solvent are needed, to alleviate the defect of low yield. When such large volumes of vessel and solvent are employed, not all of the experimental operators can run the reaction.

Taken up, in the conventional method above, the yield is about 10-15%, and deglycosylation generally occurs, which is not conducive to the subsequent massive production of 6-aminohexyl lactoside-NCS-benzyl-NODA-GA conjugate.

SUMMARY

In view of the problems above, the present invention provides a method for preparing a 6-aminohexyl lactoside-NCS-benzyl-NODA-GA conjugate. The preparation method comprises brominating perbenzoylated lactose with hydrobromic acid; glycosylating 6-azidohexanol to obtain 6-azidohexyl perbenzoyl lactoside; and deprotecting this precursor in two steps to obtain 6-aminohexyl lactoside, and conjugating 6-aminohexyl lactoside to p-NCS-benzyl-NODA-GA in triethyl amine as an alkaline solvent, to obtain a 6-aminohexyl lactoside-p-NCS-benzyl-NODA GA conjugate.

In an embodiment, the hydrobromic acid is a 33% solution of hydrobromic acid in acetic acid.

In an embodiment, the perbenzoylated lactose is prepared with benzoyl chloride in the presence of pyridine while in an ice bath.

In an embodiment, the brominating comprises dissolving perbenzoylated lactose in absolute dichloromethane; and adding hydrobromic acid slowly while in an ice bath.

In an embodiment, the 6-azidohexanol is prepared by reacting 6-bromo-1-hexanol dissolved in DMF with a $NaN_3$ solution at 80° C.

In an embodiment, the deprotecting comprises dissolving the precursor in methanol; and adding a catalytic amount of sodium methoxide, and removing the benzoyl group through reaction at 60° C.

In an embodiment, the deprotecting comprises dissolving the precursor in a co-solvent of methanol/water 1:1; and adding palladium on carbon, and removing the azido group through hydrogenation.

In an embodiment, the complexing agent for conjugation is p-NCS-benzyl-NODA-GA.

By means of the method for preparing a 6-aminohexyl lactoside-NCS-benzyl-NODA-GA conjugate according to the present invention, the 6-aminohexyl lactoside-NCS-benzyl-NODA-GA product prepared has a high stability, and a good yield. Therefore, the method is suitable for massive production.

The summary above and the detailed description of specific embodiments below of the present invention are provided for exemplifying and explaining the principle of the present invention, and for further interpreting the scope of the claims of the present invention.

BRIEF DESCRIPTION OF DRAWINGS

FIG. 1 shows the structure and preparation process of a 6-aminohexyl lactoside-NCS-benzyl-NODA-GA conjugate according to an embodiment of the present invention.

DETAILED DESCRIPTION OF DISCLOSED EMBODIMENTS

The particular features and advantages of the present invention are described in detail in implementations of the present invention below. The technical content may be understood and practiced by any skilled in the art based on the disclosure herein, and the relevant objectives and advantages of the present invention will be apparent to those skilled in the art from the following disclosure, appended claims and accompanying drawings. The embodiments below are given for further illustrating the idea of the present invention in detail, instead of limiting the scope of the present invention thereto.

The features and implementations of the present invention are detailed with preferred embodiments below.

FIG. 1 shows the structure and preparation process of a 6-aminohexyl lactoside-NCS-benzyl-NODA-GA conjugate. An embodiment of the present invention discloses a method for synthesizing 6-aminohexyl lactoside-NCS-benzyl-NODA-GA conjugate, which comprises the following steps.

S01: Benzoyl chloride is coupled to lactose, to form a compound 1: perbenzoylated lactose.

S02: The compound 1: perbenzoylated lactose is brominated with hydrobromic acid, to form a compound 2: perbenzoylated lactosyl bromide.

S03: NaN$_3$ is coupled to 6-bromo-1-hexanol, to form a compound 3: 6-azidohexanol.

S04: The compound 3: 6-azidohexanol is glycosylated with the compound 2: perbenzoylated lactosyl bromide in the presence of a catalyst in a solvent, to form a compound 4: 6-azidohexyl-perbenzoyl lactoside compound, where the catalyst is AgOTf.

S05: The compound 4 is deprotected by removing the benzoyl protecting group in the presence of sodium methoxide, to form a compound 5: 6-azidohexyl lactoside compound.

S06: The compound 5 is hydrogenated in the presence of a catalyst, to remove the azido protecting group, and form a compound 6: 6-aminohexyl lactoside, wherein the catalyst is 10% palladium on activated carbon.

S07: The compound 6 is conjugated to p-NCS-benzyl-NODA-GA in triethyl amine as an alkaline solvent, to form a compound 7: 6-aminohexyl lactoside-NCS-benzyl-NODA-GA conjugate.

Example I. Preparation of 6-Aminohexyl Lactoside with Protection Implemented Through Acetylation with Acetic Anhydride in the Presence of Pyridine The reaction route was as shown in Scheme I below, in which 6-aminohexyl lactoside was prepared with protection implemented through acetylation with acetic anhydride in the presence of pyridine.

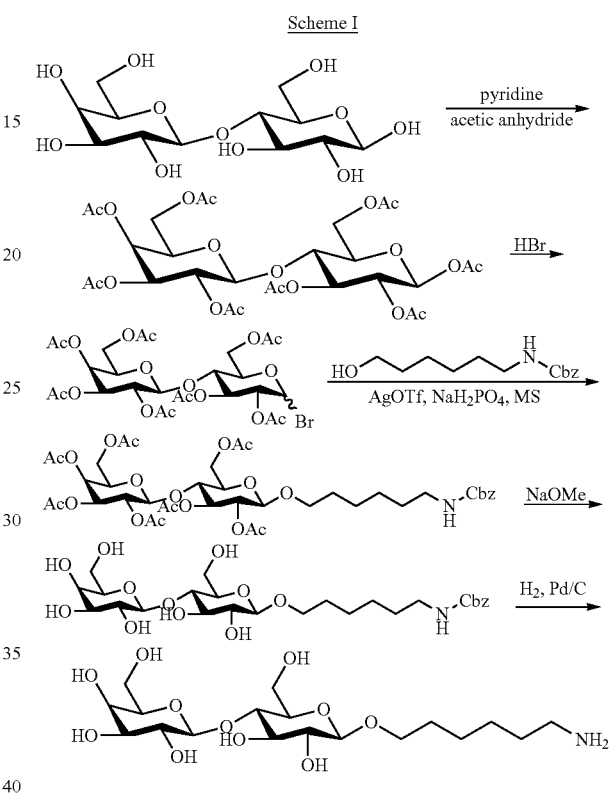

Scheme I

Lactose (6.61 g, 18.35 mmol) was added to a 250 mL round-bottom reaction flask, a magnetic stirrer was placed, and then pyridine (180 mL) was added. The suspension was transferred to an ice bath and stirred. Then, acetic anhydride (80 mL) was slowly added to the reaction flask, and stirred for 10 min while in the ice bath. Subsequently, the reaction flask was removed from the ice bath and the reaction was continued for 18 hrs under a nitrogen atmosphere at room temperature. After reaction, the suspension became a slight yellow clear solution. Then, ethyl acetate (300 mL) was added and the solution in the reaction flask was transferred to an extractor. Pyridine in the organic layer was extracted into the aqueous layer with 1 M aqueous hydrochloric acid solution (150 mL×3). Then, acetic acid in the organic layer was extracted into the aqueous layer with a saturated aqueous sodium bicarbonate solution (150 mL×2). Finally, the organic layer was washed with saturated saline (100 mL×1). The organic layer was collected into a conical flask, and magnesium sulfate was added to remove the remaining water in the organic phase. Afterwards, the salts were removed by filtering, the solvent was removed by concentration under reduced pressure (in a water bath at 50° C.), and the residue was dried under high vacuum, to obtain 12.38 g of an α- and β-acetyl lactose mixture as a vesicular gel (Yield 99%). Then bromination was carried out as follows. The peracetyl lactose (1.01 g, 1.49 mmol) was added to a 50 mL round-bottom reaction flask, a magnetic stirrer was placed, and then absolute dichloromethane (16 mL) was added. Next, the reaction flask was transferred to an ice bath and stirred. Hydrobromic acid (33% in acetic acid, 2.0 mL) was added slowly. The reaction was continued for 10 min while the reaction flask was in the ice bath. Then, the reaction flask was removed from the ice bath and the reaction was continued for 5 hrs under a nitrogen atmosphere at room temperature. During the reaction process, the color of the solution changed from dark orange to brown. After reaction, ethyl acetate (120 mL) was added and the solution was transferred to an extractor. The organic layer was washed with a saturated sodium bicarbonate solution (50 mL×1) to remove hydrobromic acid and acetic acid, and then washed with water (100 mL×1) and saturated saline (50 mL×1). The organic layer was collected into a conical flask, and magnesium sulfate was added to remove the remaining water in the organic phase. The salts were removed by filtering, and then the solvent was largely removed by concentration under reduced pressure (in a water bath at 40° C.), to obtain a light yellow oil. Then, diethyl ether (80 mL) was added and shaken vigorously until uniform. A white solid product was precipitated out, which was filtered using a Buchner funnel, and rinsed with a small amount of ice-cold diethyl ether. The white solid was collected and dried for 2 hrs under high vacuum, to obtain 0.79 g of pracetyl lactosyl bromide (Yield 76%). It should be noted that the compound needs to be stored in a sealed condition for a not long period of time, and used in subsequent reactions in 1 week after preparation.

Peracetyl lactosyl bromide (18.75 g, 26.80 mmol) was reacted with N-benzyloxycarbonyl-6-amino-1-hexanol (Cbz-aminohexanol) (10.08 g, 40.11 mmol) in a 500 mL two-neck reaction flask, and dried for 2 hrs under high vacuum. In this example, the reaction may be monitored through UV absorption of Cbz on Cbz-aminohexanol by using a UV lamp, and Cbz is readily to be removed through hydrogenation. After drying, nitrogen was introduced via one neck, and absolute dichloromethane (200 mL), $Na_2HPO_4$ (7.2 g, 50.72 mmol), and activated molecular sieve (4 Å MS, about 11 g) were sequentially added to the reaction flask. The reaction flask was transferred to an ice bath and stirred. AgOTf (8.37 g, 32.58 mmol) was slowly added via the other neck of the reaction flask under a positive-pressure nitrogen atmosphere. After addition, a rubber stopper was plugged. The reaction flask was removed from the ice bath and the reaction was continued for 5 hrs under a nitrogen atmosphere at room temperature. During the reaction process, a yellow solid (AgBr) was precipitated out in the reaction flask, and then a grayish brown suspension was gradually formed. After reaction, celite was laid on a G3 suction funnel, and filtration was conducted under reduced pressure. The solid was rinsed with a small amount of ethyl acetate (about 20 mL×3), the filtrate was collected, and the solvent was largely removed by concentration under reduced pressure. After concentration, ethyl acetate (400 mL) was added and transferred to an extractor. The organic phase was washed with 1 M HCl (150 mL×2), followed by saturated sodium bicarbonate (150 mL×1), water (100 mL×1), and saturated saline (100 mL×1). The organic layer was removed of the remaining water by using magnesium sulfate, filtered, and concentrated under reduced pressure to largely remove the solvent. The crude product was preliminarily separated by short silica gel column chromatography (ethyl acetate/toluene 5:5), to obtain 3.52 g of Cbz-aminohexyl-peracetylated lactose. It should be noted that because the results from column chromatography of Cbz-aminohexyl-peracetylated lactose was quite close to that of peracetyl lactosyl bromide, Cbz-aminohexyl-peracetylated lactose was directly used in the following hydrolysis reaction before purification.

Cbz-aminohexyl-peracetylated lactose (3.52 g) was dissolved in absolute methanol (32 mL). Then, a solution of sodium methoxide in methanol (5.4 M, 1.3 mL) was added and reacted for 3 hrs at room temperature. After reaction, an acidic resin (Dowex® 50WX8) was slowly added, and the pH value was adjusted to approximate neutral range by real-time monitoring with general-purpose pH paper. Then, the acidic resin was removed by filtration under reduced pressure, the filtrate was collected, and the solvent was removed by concentration under reduced pressure. The residue was purified by reversed phase chromatography (RP-18) using an automatic rapid preparative separation system, eluting with 50% methanol in water at a flow rate of 26 mL/min and with detection at a wavelength of 254 nm. After separation by chromatography, the product was collected, concentrated under reduced pressure (in a water bath at 50° C.), and dried under high vacuum, to obtain 2.26 g of a product with a single lactoside backbone as a white solid (Yield 15%). Hydrogenation afforded equivalent amount of 6-aminohexyl lactoside, with which however, deglycosylated side product was usually concomitantly present.

Example 2. Preparation of 6-Aminohexyl Lactoside with Protection Implemented Through Acetylation with Acetic Anhydride in the Presence of Iodine The reaction route was as shown in Scheme II below, in which 6-aminohexyl lactoside was prepared with protection implemented through acetylation with acetic anhydride in the presence of iodine.

Scheme II

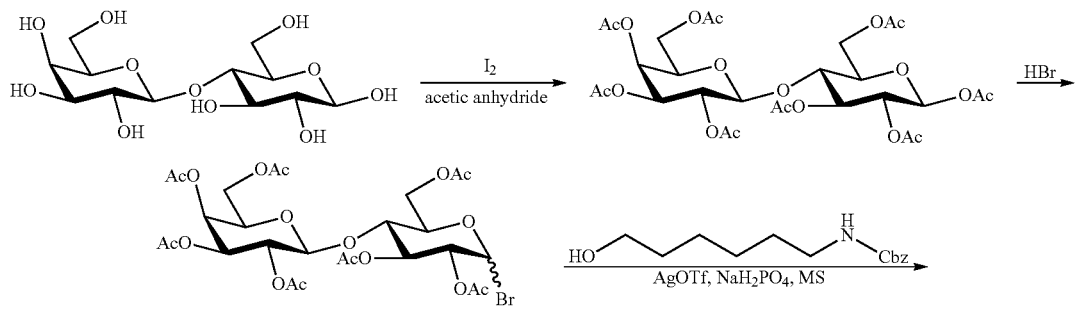

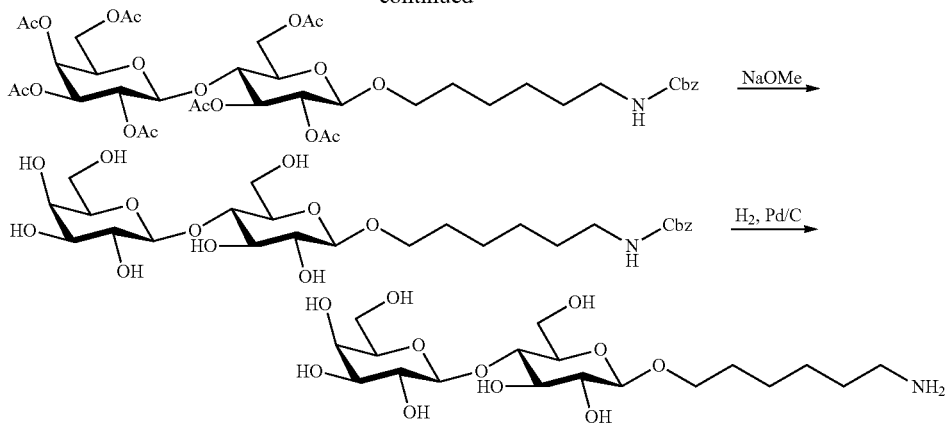

Lactose (1.0 equiv, 60.0 g, 175.3 mmol) was added to a 500 mL reaction flask, a stirrer was placed, and then acetic anhydride (12 equiv, 198 mL, 2.10 mol) was added. The reaction flask was positioned in cold water and stirred for 30 min. Then, $I_2$ (50 mg/g sugar, 3 g) was added. The reaction was continued for 6 hrs under a nitrogen atmosphere while in a water bath. After the reaction was complete as detected by TLC (upon which the solution appeared dark black), the solution was transferred to an extractor, to which EtOAc (500 mL) was added, and extracted with saturated $Na_2S_2O_3$ $_{(aq)}$ (300 mL×4). The dark black solution became a light yellow clear solution. Then, the organic layer was collected, and extracted respectively with saturated $NaCl_{(aq)}$ (300 mL), and saturated $NaHCO_{3(aq)}$ (300 mL×4). The organic layer was collected, removed of water with $Na_2SO_4$, filtered, concentrated under reduced pressure, and dried under high vacuum, to obtain 104.0 g of peracetyl lactose as a slight brown vesicular gel. Then peracetyl lactose was brominated as follows. The peracetyl lactose (1.0 equiv, 90.0 g, 0.133 mol) was dissolved in absolute $CH_2Cl_2$ (500 mL) in a 1 L round-bottom reaction flask. Subsequently, HBr (33% in acetic acid) (150 mL) was added to the reaction flask while in an ice bath, reacted for 20 min while in the ice bath, and then for 4 hrs at room temperature. After the reaction was complete as detected by TLC, $CH_2Cl_2$ (100 mL) was added, and transferred to an extractor. The organic layer was extracted respectively with saturated $NaHCO_{3(aq)}$ (300 mL×2) and saturated $NaCl_{(aq)}$ (200 mL). The organic layer was collected, removed of water with $MgSO_4$, and filtered. The solvent was largely removed by concentration under reduced pressure. Diethyl ether (700 mL) was added and shaken vigorously until uniform. A white solid product was precipitated out, which was filtered, and rinsed with a small amount of ice-cold diethyl ether. The white solid was collected and dried for 2 hrs under high vacuum, to obtain 23.63 g of peracetyl lactosyl bromide.

Next, peracetyl lactosyl bromide (1.0 equiv, 54.0 g, 77.2 mmol) was dried for 2 hrs with Cbz-aminohexanol (1.5 equiv, 29.1 g, 115.8 mmol) in a 1 L reaction flask under high vacuum. Absolute $CH_2Cl_2$ (500 mL), $Na_2HPO_4$ (2.0 equiv, 21.9 g, 154.4 mmol), and activated molecular sieve (4 Å MS, about 35 g) were sequentially added to the reaction flask. Then, the reaction flask was transferred to an ice bath and stirred for 30 min. Finally, AgOTf (1.2 equiv, 23.8 g, 92.6 mmol) was slowly added under a nitrogen atmosphere. The reaction was transferred to room temperature, and continued for 5 hrs under a nitrogen atmosphere. After reaction, the solution was filtered through celite on a G3 suction funnel under reduced pressure. The solid was rinsed with a small amount of EtOAc (50 mL×3). The filtrate was concentrated under reduced pressure to largely remove the solvent. EtOAc (600 mL) was added, and transferred to an extractor. The organic phase was washed respectively with 1M HCl (300 mL×2), and then saturated $NaHCO_{3(aq)}$ (300 mL×1), water (100 mL×1), and saturated $NaCl_{(aq)}$(100 mL). The organic layer was collected, removed of water with $MgSO_4$, filtered, and concentrated under reduced pressure to largely remove the solvent. The crude product was preliminarily separated by short silica gel column chromatography (EtOAc:toluene=5:5), to obtain 4.52 g of Cbz-aminohexyl-peracetyl lactoside. Deglycosylated side product was present in the product. After deacetylation, the purification was difficult, and the yield was only 5%. During the process, attempt was made to replace AgOTf by $Ag_2CO_3$. However, deglycosylated side product was still produced upon glycosylation, causing large difficulty in purification after reaction. The glycosylation was also carried out with benzyl-Cbz-aminohexanol, and delactosylation occurred to the resulting single-chain benzyl Cbz-aminohexyl-peracetyl lactoside upon removing the acetyl protecting group, which was assumed to be a result caused by molecular conformation. Therefore, a new process in which lactose was protected with groups other than acetyl was attempted.

Example 3. Preparation of 6-Aminohexyl Lactoside with Protection Implemented Through Benzoylation with Benzoyl Chloride in the Presence of Pyridine The reaction route was as shown in Scheme III below, in which 6-aminohexyl lactoside was prepared with protection implemented through benzoylation with benzoyl chloride in the presence of pyridine.

Scheme III

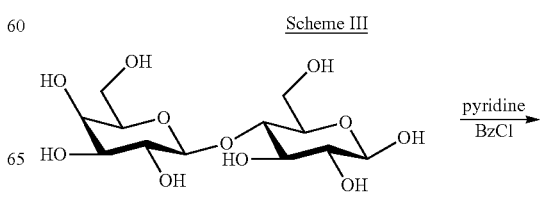

-continued

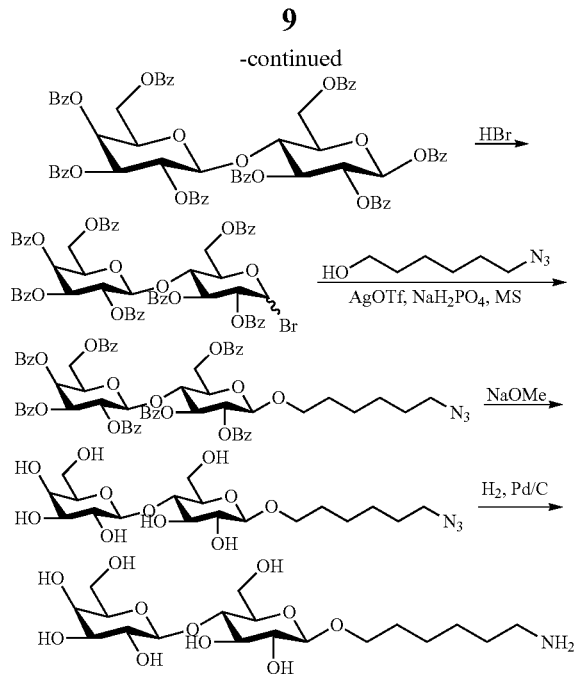

Lactose (1.0 equiv, 15.0 g, 48.8 mmol) was added to a 500 mL reaction flask, a stirrer was placed, and then pyridine (38.0 equiv, 150 mL, 1.86 mol), benzoyl chloride (13.0 equiv, 53.0 mL, 64.0 mol) and DMAP (dimethyl aminopyridine, 0.01 equiv, 100 mg, 0.8 mmol) were added in sequence and stirred for 4 hrs at room temperature. The solution was transferred to an extractor, to which EtOAc (200 mL) was added and extracted with saturated NaHCO$_{3(aq)}$ (300 mL×2). The organic layer was collected, removed of water with MgSO$_4$, filtered, concentrated under reduced pressure, and dried under high vacuum, to obtain 38.8 g of a cream white solid. Perbenzoyl lactose (1.0 equiv, 20.0 g, 17.0 mmol) was dissolved in dichloromethane (70 mL), and HBr (33% in acetic acid) (17.5 mL) was added and stirred for 4 hrs at room temperature. The solution was transferred to an extractor, to which dichloromethane (200 mL) was added and extracted with saturated NaHCO$_{3(aq)}$ (300 mL×2). The organic layer was collected, removed of water with MgSO$_4$, filtered, concentrated under reduced pressure, and dried under high vacuum, to obtain 18.7 g of a cream white solid.

Next, perbenzoyl lactosyl bromide (1.0 equiv, 6.0 g, 5.3 mmol), 6-azidohexanol (1.5 equiv, 1.2 mL, 8.0 mmol), a molecular sieve (1.1 g) and dichloromethane (12 mL) were added. AgOTf (1.5 equiv, 2.1 g, 8.2 mmol) was added at −78° C. and then stirred for 5 hrs. After reaction, the solution was filtered through celite on a G3 suction funnel under reduced pressure. The solid was rinsed with a small amount of EtOAc (50 mL×3). The filtrate was concentrated under reduced pressure to largely remove the solvent. EtOAc (150 mL) was added, and transferred to an extractor. The organic phase was washed respectively with 1 M HCl (100 mL×2), and then saturated NaHCO$_{3(aq)}$ (100 mL×1), water (100 mL×1), and saturated NaCl$_{(aq)}$(100 mL×1). The organic layer was collected, removed of water with MgSO$_4$, filtered, and concentrated under reduced pressure to largely remove the solvent. The crude product was preliminarily separated by short silica gel column chromatography (EtOAc:toluene=1:9), to obtain 3.3 g of 6-azidohexyl perbenzoyl lactoside. Then, of 6-azidohexyl perbenzoyl lactoside (3.3 g) was dissolved in methanol (50 mL), and then NaOMe (3 mg) was added and stirred for 3 hrs at 60° C. An acidic resin (Amberlite IR-120 resin (H$^+$)) was slowly added, and the pH value was adjusted to approximate neutral range by real-time monitoring with general-purpose pH paper. Then, the acidic resin was removed by filtration under reduced pressure, the filtrate was collected, and the solvent was removed by concentration under reduced pressure. Acetone (100 mL) was added, and a solid was collected by filtration under reduced pressure. The solid was dissolved in methanol-water (1:1, 20 mL), Pd/C (10 mg) was added, and stirred for 5 hrs under a nitrogen atmosphere. After filtration under reduced pressure and removal of the solvent by concentration under reduced pressure, 6-aminohexyl lactoside (1.1 g) was obtained.

In synthesis route was as shown in Scheme III. In the preparation process in this example, the starting lactose was protected by benzoylation with benzoyl chloride in the presence of pyridine. Then, bromination was conducted by adding a 33% solution of hydrobromic acid in acetic acid, to obtain a brominated compound bearing a benzoyl protecting group. The compound was reacted with 6-azidohexanol in the presence of AgOTf and a molecular sieve, and then the resulting product was deprotected by removing the benzoyl and azido group, to obtain single-chain 6-aminohexyl lactoside. In the preparation process of this example, no deglycosylation occurs, the yield is approximately increased to 44%, and the target product may be successfully synthesized after conjugating to NOTA.

Analytic data of compound: C$_{18}$H$_{35}$NO$_{11}$; PR-TLC (MeOH/1% TFA=5:5) R$_f$=0.64; $^1$H NMR (300 MHz, CD$_3$OD) δ 4.46 (1H, d, J=7.2 Hz), 4.28 (1H, d, J=7.8 Hz), 3.92-3.67 (7H, m), 3.60-3.38 (7H, m), 3.23 (1H, t, J=7.8 Hz), 2.78 (1H, t, J=7.8 Hz), 1.67-1.56 (4H, m), 1.43-1.40 (4H, m); $^{13}$C NMR (75 MHz, CD$_3$OD) δ 103.93, 103.05, 79.56, 75.91, 75.33, 75.26, 73.64, 73.60, 71.39, 69.53, 69.11, 61.33, 60.76, 40.30, 29.68, 29.35, 26.25, 25.55; ESI-MS: calcd for 442.22. found: m/z 442.22 [M+H]$^+$.

Example 4: Synthesis of 6-Aminohexyl Lactoside-NOTA Conjugate

The synthesis route was as shown in Scheme IV below. 6-aminohexyl lactoside was conjugated to NCS-benzyl-NODA GA as follows.

Scheme IV

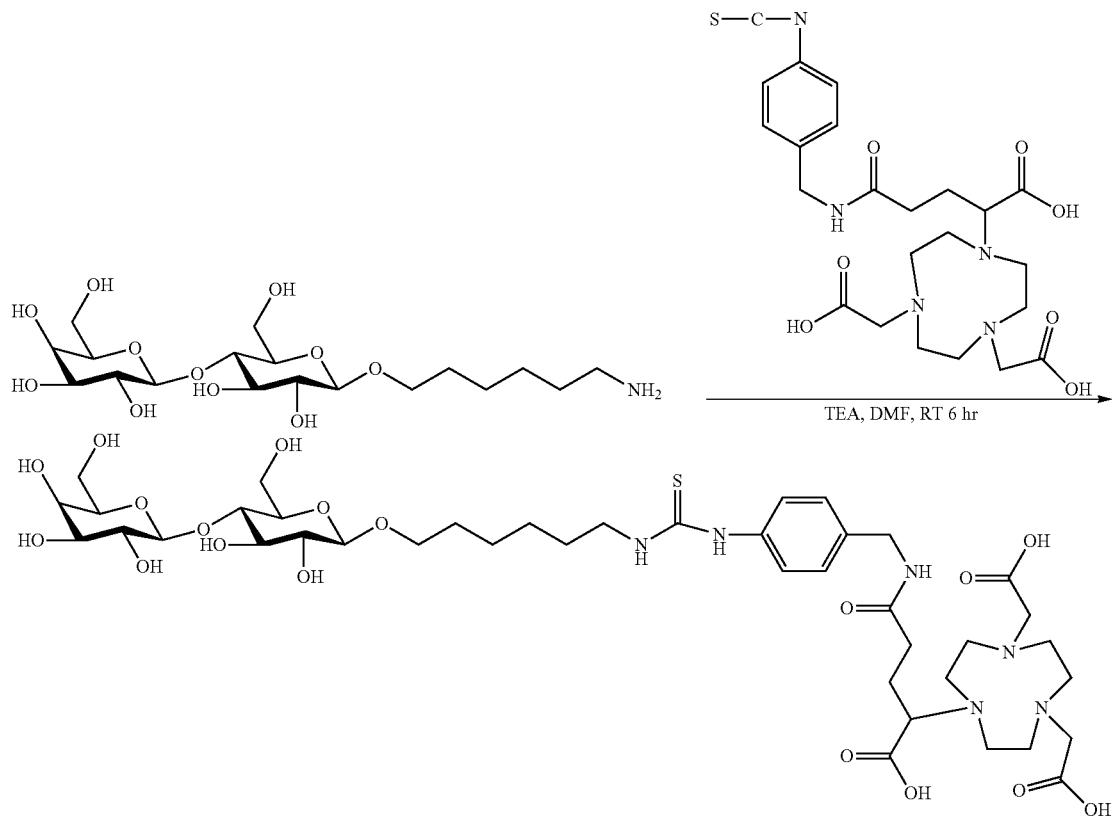

6-aminohexyl lactoside (10 μmol) was dissolved in TEA/DMF (0.1 mL/1 mL), and then p-NCS-benzyl-NODA GA (20 μmol, CheMatech, France. FW=521.59) was added and reacted for 6 hrs with stirring. Diethyl ether (30 mL) was added, and a solid was precipitated out. Then supernatant was decanted off, and then additional diethyl ether (30 mL) was added, sonicated for 5 min and centrifuged. Then supernatant was decanted off, and a crude solid product was obtained. The crude product was purified using an automatic rapid preparative separation system, concentrated under reduced pressure, and lyophilized, to obtain 6-aminohexyl lactoside-NCS-benzyl-NODA GA (6 μmol) (Yield: about 60%).

Analytic data of compound: $C_{41}H_{66}N_6O_{18}S$; ESI-MS: calcd for 963.42. found: m/z 963.42 $[M+H]^+$.

Example 5: Preparation of 6-Cbz-hexanol

The synthesis route was as shown in Scheme V below. Cbz-aminohexanol was prepared as follows.

Scheme V

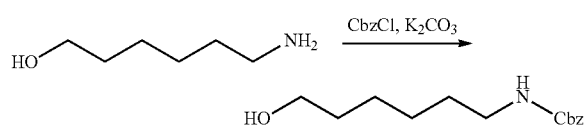

6-aminohexanol (8.30 g, 70.8 mmol) and potassium carbonate (5.86 g, 40.2 mmol) was added to a 100 mL round-bottom reaction flask, a magnetic stir was placed, and then water (35 mL) was added and stirred vigorously. Then, benzyl chloroformate (CbzCl; 12.1 g, 70.9 mmol) dissolved in diethyl ether (12 mL) was slowly added dropwise, and reacted overnight at room temperature (about 15 hrs, during which a white particle-like was precipitated out). After reaction, the solution was filtered through a G3 suction funnel under reduced pressure. The solid was rinsed with a small amount of water (about 20 mL) and hexane (about 30 mL). The solid was collected, dissolved in ethyl acetate (300 mL), and transferred to an extractor. The organic phase was washed with 1 M HCl (200 mL×1) and saturated saline (200 mL×1). The organic phase was removed of remaining water over magnesium sulfate, filtered, concentrated under reduced pressure (in a water bath at 45° C.) and dried under high vacuum, to obtain 13.3 g of a white solid product (Yield: 74%).

Analytic Data of Compound:

$C_{14}H_{21}NO_3$; TLC (EtOAc/toluene=5:5) $R_f$=0.41; $^1$H NMR (300 MHz, CDCl$_3$) δ 7.37-7.28 (5H, m), 5.09 (2H, s), 4.77 (1H, br), 3.63 (2H, q, J=6.3 Hz), 3.20 (2H, q, J=6.6 Hz), 1.58-1.36 (9H, m); ESI-MS: calcd for 252.15. found: m/z 252.16 $[M+H]^+$.

Example VI: Preparation of Benzyl Cbz-Aminohexanol

The synthesis route was as shown in Scheme VI below. Benzyl Cbz-aminohexanol was prepared as follows.

Scheme VI

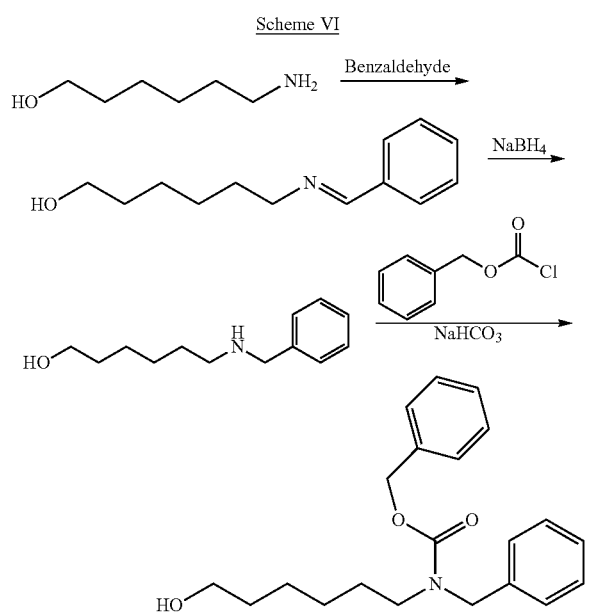

6-amino-1-hexanol (1.0 equiv, 8.30 g, 70.8 mmol) and EtOH (100 mL) was added to a 250 mL reaction flask, and then benzaldehyde (1.01 equiv, 7.3 mL, 71.5 mmol) was slowly added under a nitrogen atmosphere, and reacted for 16 hrs at 50° C., during which the reaction was monitored by TLC (developing with EtOAc:toluene=4:6) in combination with ninhydrin). After the reaction was detected to be complete, the solvent was removed under reduced pressure. The intermediate was transferred to a 250 mL two-neck flask, and 150 mL of MeOH was added and stirred for 10 min while in ice bath. Subsequently, NaBH$_4$ (1.15 equiv, 3.1 g, 81.4 mmol) was slowly added under a nitrogen atmosphere. After addition, the reaction flask was naturally warmed and reacted for 2 hrs. The remaining NaBH$_4$ in the reaction flask was quenched, ethanol (3.3 ml, 56.7 mmol) was slowly added, and then saturated NaHCO$_{3(aq)}$ (100 mL) was added and stirred for 30 min. Finally, the aqueous layer was extracted twice with diethyl ether (300 mL). The organic layer was collected, and concentrated under reduced pressure to 200 mL. Water (100 mL) and NaHCO$_3$ (10.7 g, 127 mmol) was added to the organic layer. Finally, CbzCl (1.05 equiv, 10.6 mL, 7.44 mmol) was slowly added to the reaction flask, and reacted for 14 hrs at room temperature. Diethyl ether (150 mL) was additionally added to the mixed solution, and the aqueous layer was discarded. The organic layer was extracted respectively with 1 M HCl$_{(aq)}$ (200 mL×1) and saturated NaCl$_{(aq)}$ (200 mL×1). The organic phase was collected, removed of water with MgSO$_4$, filtered, and concentrated under reduced pressure, to obtain a yellow oil.

Example VII: Preparation of 6-Azidohexanol

The synthesis route was as shown in Scheme VII below. 6-azidohexanol was prepared as follows.

Scheme VII

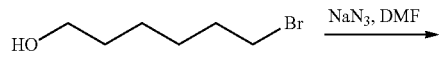

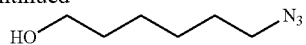

The commercially available starting 6-bromo-1-hexanol (1.0 equiv, 7.2 g, 10 mL, 39.9 mmol) was dissolved in DMF (40 mL), added to a 100 mL round-bottom flask, and adding a solution of NaN$_3$ in H$_2$O (30 mL, 3.0 equiv, 9.1 g, 120 mmol). The reaction flask was placed in an oil bath, heated to 80° C., and reacted for 24 hrs. After the reaction was complete (upon which the solution appeared light yellow), the reaction flask was warmed to room temperature. Saturated NaCl$_{(aq)}$ (120 mL) was added, and extracted with n-hexane (100 mL×3). The organic layer was collected, removed of water with Na$_2$SO$_4$, filtered, concentrated under reduced pressure, and suction dried.

Analytic data of compound: C$_6$H$_{13}$N$_3$O; TLC (EtOAc/Hexane=3:7) R$_f$=0.5; $^1$H NMR (300 MHz, CD$_3$OD) δ 3.66-3.62 (2H, t, J=6.0 Hz), 3.30-3.25 (2H, t, J=6.9 Hz), 1.67-1.54 (4H, m), 1.46-1.36 (4H, m); $^{13}$C NMR (75 MHz, CD$_3$OD) δ 62.64, 51.35, 32.50, 28.771, 26.49, 25.30.

Although embodiments of the present invention are illustrated and described as above, various modifications and improvements may be made by those skilled in the art. The present invention is not intended to be limited to particular forms described and any modifications made without departing from the spirit and scope of the present invention fall within the scope as defined by the appended claims.

By means of the method for preparing 6-aminohexyl lactoside according to the present invention, the 6-aminohexyl lactoside product prepared has a high stability, and a good yield. Therefore, the method is suitable for massive production.

In summary, the features of the present invention, as a whole or in any combination thereof are neither found in the same type of products, nor previously disclosed, thus meeting the requirements of the patent law. Therefore, this patent of invention is filed in accordance with the patent law.

Embodiments of the present invention are disclosed as above; however, the present invention is not limited thereto. Many variations may be made by any one of skills in the art based on the shape, structure, feature, and spirit described in the claims without departing from the spirit and scope of the present invention. Therefore, the protection scope of the present invention is as defined by the appended claims.

What is claimed is:

1. A method for preparing a 6-aminohexyl lactoside-NOTA conjugate, comprising:
   brominating perbenzoylated lactose with hydrobromic acid;
   glycosylating 6-azidohexanol to obtain a precursor; and
   deprotecting the precursor in two steps to obtain 6-aminohexyl lactoside, and conjugating 6-aminohexyl lactoside to p-NCS-benzyl-NODA-GA in triethyl amine as an alkaline solvent, to obtain a 6-aminohexyl lactoside-p-NCS-benzyl-NODA GA conjugate.

2. The preparation method according to claim 1, wherein the hydrobromic acid is a 33% solution of hydrobromic acid in acetic acid.

3. The preparation method according to claim 1, wherein the perbenzoylated lactose is prepared with benzoyl chloride in the presence of pyridine while in an ice bath.

4. The preparation method according to claim 1, wherein the brominating comprises
- dissolving perbenzoylated lactose in absolute dichloromethane; and
- adding hydrobromic acid slowly while in an ice bath.

5. The preparation method according to claim 1, wherein the 6-azidohexanol is prepared by reacting 6-bromo-1-hexanol dissolved in DMF with a $NaN_3$ solution at 80° C.

6. The preparation method according to claim 1, wherein the deprotecting comprises
- dissolving the precursor in methanol; and
- adding a catalytic amount of sodium methoxide, and removing the benzoyl group through reaction at 60° C.

7. The preparation method according to claim 1, wherein the deprotecting comprises
- dissolving the precursor in a co-solvent of methanol/water 1:1; and
- adding palladium on carbon, and removing the azido group through hydrogenation.

8. The preparation method according to claim 1, wherein the NOTA is p-NCS-benzyl-NODA-GA.

9. The preparation method according to claim 1, wherein the conjugating comprises reacting p-NCS-benzyl-NODA-GA with 6-aminohexyl lactoside for 6 hrs in triethyl amine as an alkaline solvent.

* * * * *